United States Patent [19]
Wright et al.

[11] Patent Number: 5,736,056
[45] Date of Patent: Apr. 7, 1998

[54] METHOD FOR ENHANCING BIOCIDAL ACTIVITY

[75] Inventors: J. Barry Wright; Daniel Michalopoulos, both of Jacksonville, Fla.

[73] Assignee: BetzDearborn Inc., Trevose, Pa.

[21] Appl. No.: 783,683

[22] Filed: Jan. 15, 1997

Related U.S. Application Data

[63] Continuation-in-part of Ser. No. 431,338, Apr. 28, 1995, Pat. No. 5,607,597.

[51] Int. Cl.$^6$ .................................................. C02F 1/50
[52] U.S. Cl. ........................ 210/755; 162/161; 210/764; 514/372; 514/517; 514/693; 514/727
[58] Field of Search .................... 162/161; 210/698, 210/755, 764; 422/37; 514/517, 693, 727, 372

[56] References Cited

U.S. PATENT DOCUMENTS

| | | | |
|---|---|---|---|
| 3,411,983 | 11/1968 | Girard | 210/764 |
| 4,105,431 | 8/1978 | Lewis et al. | 162/161 |
| 4,732,905 | 3/1988 | Donofrio et al. | 514/372 |

FOREIGN PATENT DOCUMENTS

| | | |
|---|---|---|
| 709376 | 5/1965 | Canada .................. 162/161 |
| 0007591 | 2/1980 | European Pat. Off. . |
| 002701 | 8/1989 | European Pat. Off. . |
| 0354889 | 8/1989 | European Pat. Off. . |
| 57-209201 | 3/1983 | Japan . |
| 63-041405 | 7/1988 | Japan . |
| 63-048202 | 7/1988 | Japan . |

OTHER PUBLICATIONS

W.K. Whitekettle, "Effects of Surface–Active Chemicals on Microbial Adhesion," *Journal of Industrial Microbiology*, 7 (1991), pp. 105–116.

S. G. Hales "Biodegredation of the Anionic Surfactant Dialkyl Sulphosuccinate" *Environmental Toxicology and Chemistry*, vol. 12, pp. 1821–1828, 1993.

*Primary Examiner*—Peter A. Hruskoci
*Attorney, Agent, or Firm*—Alexander D. Ricci; Richard A. Paikoff

[57] ABSTRACT

A treatment for enhancing the activity of biocidal compounds to control the growth of microbes in an aqueous system is disclosed, which comprises adding to said compounds an effective amount of an alkylsulfosuccinate surfactant.

16 Claims, 4 Drawing Sheets

METHOD FOR ENHANCING BIOCIDAL ACTIVITY

This application is a continuation-in-part of Ser. No. 08/431,338, filed Apr. 28, 1995 now U.S. Pat. No. 5,607,597.

BACKGROUND OF THE INVENTION

Bacterial attachment to surfaces in virtually any non-sterile aquatic environment is a well-established phenomenon. Industrial efforts to prevent colonization or to clean fouled surfaces amount to costly expenditures in a number of industrial sectors. Surfactants are regularly employed in water treatment programs as agents believed to play a role in the removal of organic masses from surfaces, in the enhancement of biocide efficacy or in the assistance in the water miscibility of various biocidal agents. Surfactants are also regularly used in the agrichemical business, particularly to enhance the action of herbicides. This is accomplished by using the surfactants to alter the surface behavior of the applied droplets, maximizing their interaction with the leaf surface.

There are numerous examples of surfactants which are able to inhibit the colonization of surfaces by inhibiting the overall growth of the organisms in the target environment. Most surfactants, regardless of class, show some inhibition of bacterial growth when used at concentrations high enough to impede surface colonization. In the water treatment industry, the most well known class of surfactants which impart a measure of colonization resistance to submerged surfaces are the cationic quaternary amine surfactants, which also function as biocides. However, even relatively mild nonionic surfactants can function in an analogous fashion. The concentration of nonionic surfactants necessary to mediate toxicity is substantially higher than for cationic surfactants, however.

Surfactants have historically been added to biocide packages because they (1) help to maintain some actives in solution which may otherwise separate and (2) help relatively hydrophobic biocides to be more miscible in an aqueous environment. Surfactants have also been considered as enhancers of the efficacy of biocides against biofilm-associated organisms by increasing the accessibility of the biocide to its cellular target.

The present invention refers to a method for enhancing the activity of biocides to control the growth of microbes in an aqueous system. The materials of the present invention have been previously used in areas such as fiber wetting in the textile industry.

DETAILED DESCRIPTION OF THE INVENTION

The present invention relates to a method for enhancing the activity of a treatment including a biocidal compound to control the growth of microbes in an aqueous system, e.g., a cooling water, pulping or papermaking system, which comprises adding to the system an effective amount of an anionic alkylsulfosuccinate surfactant. The method of the present invention allows for a decrease in the amount of biocidal compound added to the system, while maintaining the efficacy of the treatment. Thus, a more environmentally acceptable outcome is achieved, in that less biocidal material may be used while still achieving the same level of efficacy.

The method of the present invention will allow for a decrease in the amount of biocide fed to a system, without decreasing the efficacy of a particular treatment protocol.

The biocides tested in the present invention were an isothiazolinone (specifically, a mixture of 5-chloro-2-methyl-4-isothiazolin-3-one and 2-methyl-4-isothiazolin-3-one, sold as Kathon® 886F, available from Rohm and Haas Co.) and 2-bromo-2-nitropropane-1,3-diol, or BNPD (available from Boots Chemical, Pte.). Additional biocides tested in the present invention include 2,2-dibromo-3-nitriloproprionamide (DBNPA), 5-oxo-3, 4-dichloro-1,2-dithiol (dithiol) and glutaraldehyde (glut). These materials are all commercially available. The isothiazolinone compound is considered to be the preferred biocide active for the present invention, but the present invention is not limited to use of that biocide. The primary organism chosen for these studies was *Pseudomonas pickettii*, a bacterial species, although it is anticipated that the present invention will be effective against other microorganisms, e.g., fungi. The initial screening of the biocides with and without surfactant was carried out using 48 ppm (active) of surfactant, and the surfactants chosen for these experiments were the sulfosuccinates.

Figure 1:
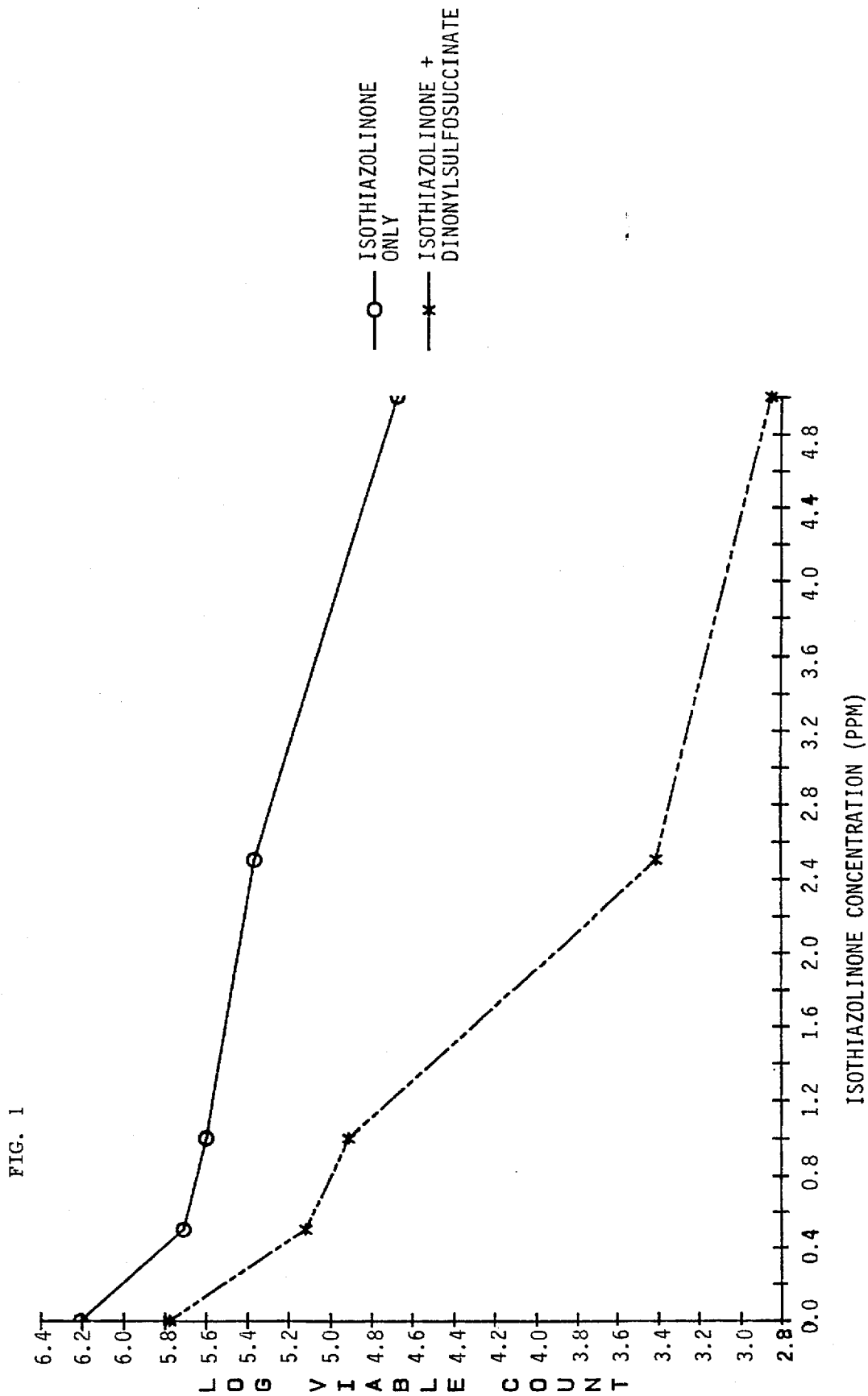
FIG. 1 illustrates isothiazolinone efficacy enhancement by 12 ppm dinonylsulfosuccinate against planktonic *P. pickettii*.
Figure 2:
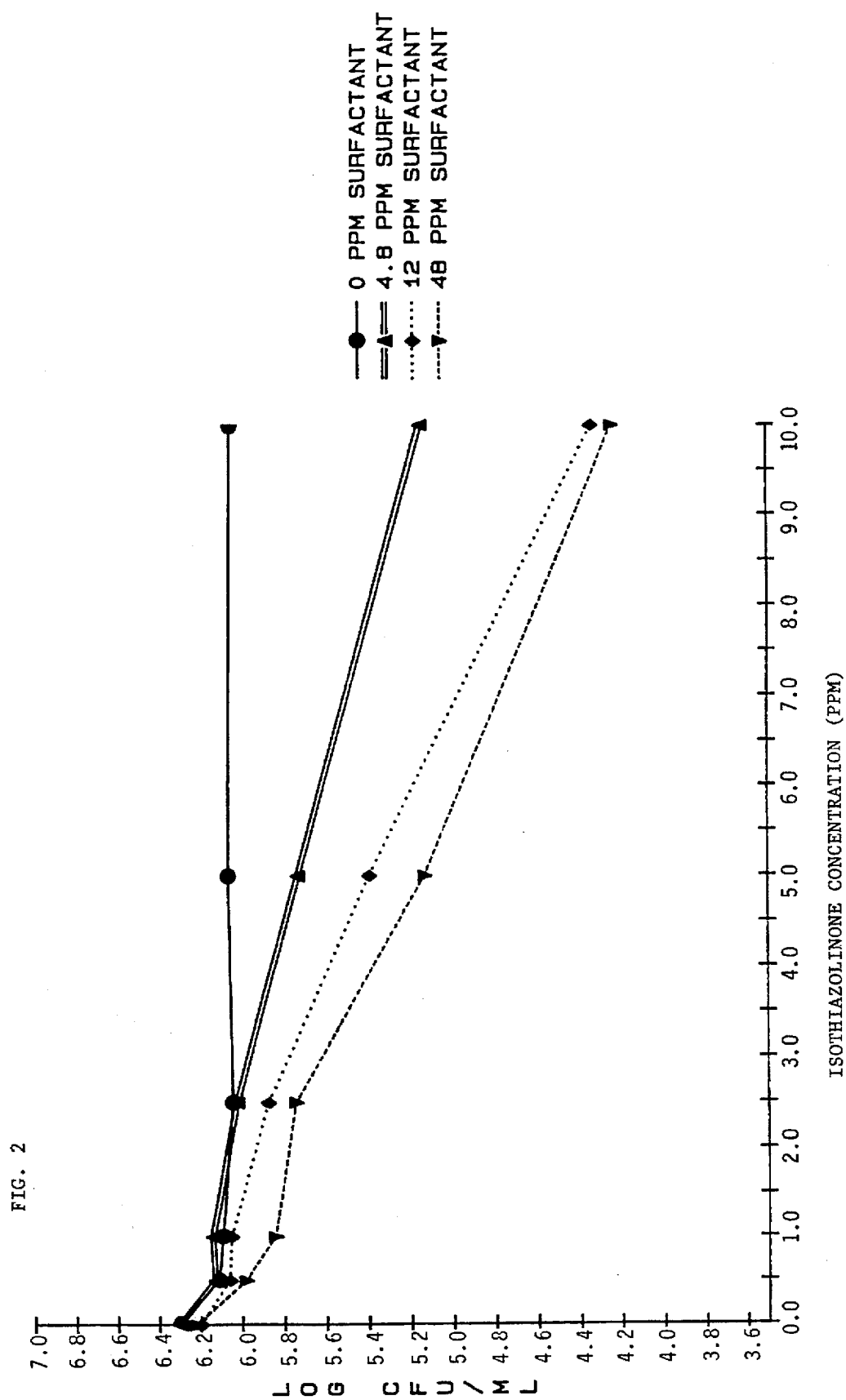
FIG. 2 illustrates dinonylsulfosuccinate enhancement of isothiazolinone efficacy against planktonic *P. pickettii*, at varying concentrations of dinonylsulfosuccinate.

The preferred sulfosuccinates, dioctylsulfosuccinate and dinonylsulfosuccinate, demonstrated a significant enhancement of the activity of BNPD. In addition, a surprisingly significant increase in the efficacy of the isothiazolinone compound (Kathon 886F) in the presence of dinonylsulfosuccinate is shown in FIG. 1. Dose-response curves demonstrated that as little as 5 ppm (active) of the dinonylsulfosuccinate compound would enhance isothiazolinone efficacy. The data also demonstrate that a near maximal increase in efficacy may be attained with as little as 12 ppm (active) of the dinonylsulfosuccinate (FIG. 2). This effect is seen as an enhancement of isothiazolinone activity, as the surfactant, alone, did not mediate significant toxicity upon the bacterial population.

Figure 3:
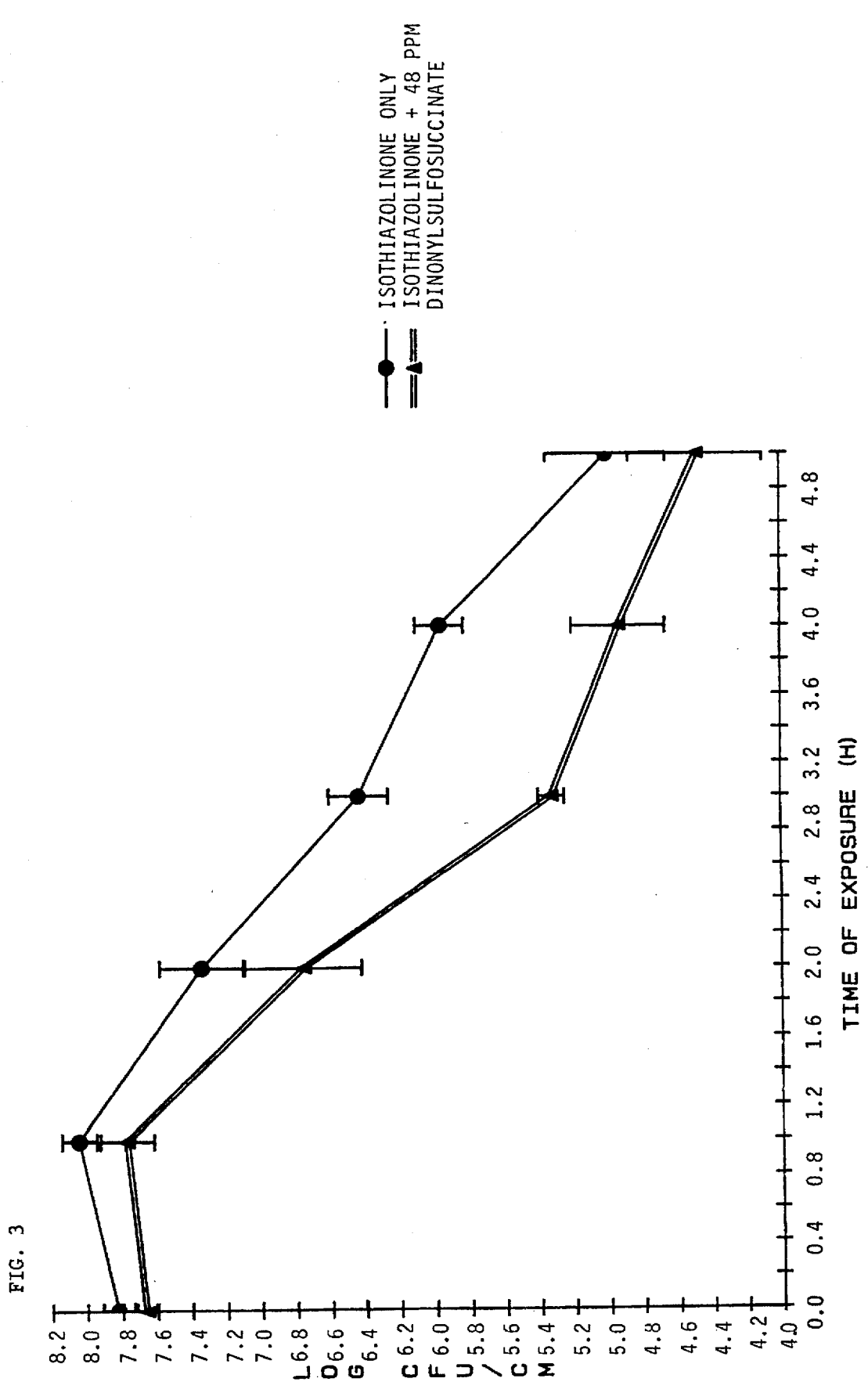
FIG. 3 illustrates the dinonylsulfosuccinate enhancement of 2 ppm isothiazolinone against sessile populations of *P. pickettii*.

In order to further evaluate the effectiveness of the alkylsulfosuccinate and biocide against sessile populations, efficacy trials in a recirculation device were conducted. Colonization in the absence of any antimicrobial or surfactant was allowed to proceed for two days, followed by the removal of the majority of the bacterial culture. The culture was replaced with either fresh media and biocide (control) or media with the addition of the appropriate amount of biocide and surfactant. The addition of a dinonylsulfosuccinate to about 2 ppm of isothiazolinone compound (Kathon 886F) greatly reduced the number of viable bacteria which could be recovered from colonized surfaces relative to the corresponding control (isothiazolinone only) surfaces (FIG. 3). Other studies demonstrated that in the absence of any antimicrobial there was not a loss of adherent bacteria from the surfaces over the same time period.

The following classes of compounds were tested, the number in parentheses indicating the carbon chain length on each ester chain: diisobutylsulfosuccinate (4); diisoamylsulfosuccinate (5); dihexylsulfosuccinate (6); dioctylsulfosuccinate (8); dinonylsulfosuccinate (9); and bistridecylsulfosuccinate (13).

Figure 4:
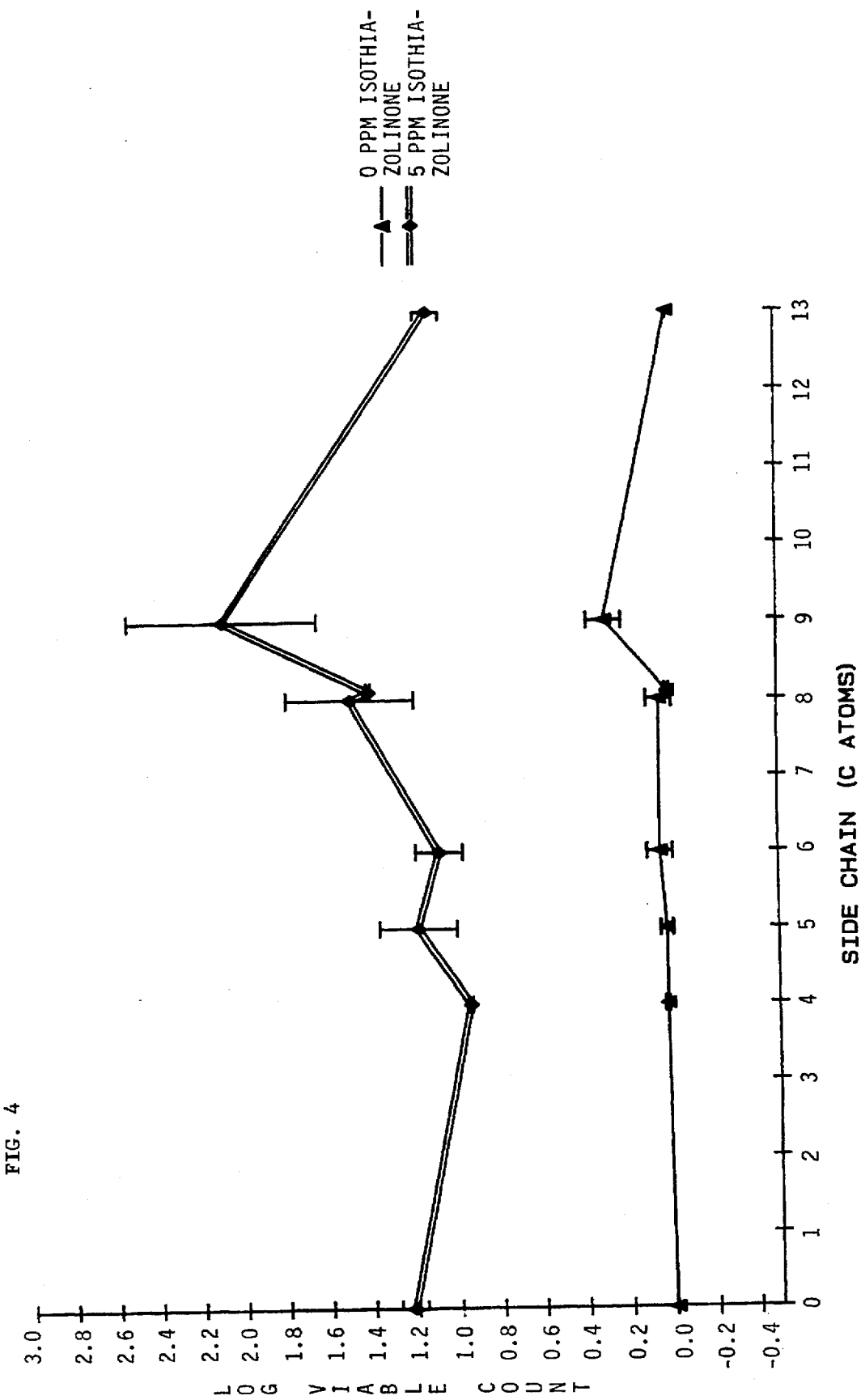
FIG. 4 illustrates alkylsulfosuccinate alkyl chain length vs. reduction in viable count of planktonic *P. pickettii* at 48 ppm concentration of surfactant.

In reference to FIG. 4, note that the 8 carbon chain length diesters were nearly as effective as the 9 carbon chain length diester compounds. Note also the increased efficacy with increased side-chain length up to 9 carbons. When the side-chain has a 13-C alkyl group there appears to be a loss of efficacy.

The concentrations of isothiazolinone compound (Kathon 886F) used throughout these experiments, particularly the ones where efficacy against P. pickettii was being examined, was quite high (about 5 ppm). This is a reflection of the relative resistance of this organism to the isothiazolinone compound. Similar experiments were conducted using P. aeruginosa in which similar results were obtained with significantly lower concentrations of isothiazolinone.

Table 1 demonstrates the enhancement of inhibition of growth of bacteria observed with Kathon and BNPD. These results were obtained using P. pickettii. Results were generated by observing the reduction in the viable counts of the bacteria, and show a significant enhancement in the efficacy of both actives (isothiazolinone and BNPD) in the presence of the $C_8$ and $C_9$ sulfosuccinates. Isothiazolinone and BNPD results are at a contact time of 3 hours.

TABLE 1

Sulfosuccinate Enhancement of Kathon and BNPD

| | $Log_{10}$ Reduction of CFU/ml | | |
|---|---|---|---|
| Surfactant (12 ppm) | 0 ppm Biocide | 5 ppm Iso[1] | 10 ppm BNPD[2] |
| None | 0.00 | 0.99 | 1.56 |
| C6-sulfosuccinate | 0.00 | 1.10 | 1.56 |
| C8-sulfosuccinate | 0.08 | 4.02 | 2.14 |
| C9-sulfosuccinate | 0.13 | 3.45 | 2.25 |
| C10-sulfosuccinate | 0.04 | 1.01 | 1.13 |

[1]Iso = isothiazolinone
[2]BNPD = 2-bromo-2-nitropropane-1,3-diol

Table 2 demonstrates the enhancement of inhibition of growth of bacteria observed with glutaraldehyde and DBNPA. These results were also obtained using P. picketii. As noted below, the results demonstrate an increase in the efficacy of the two active compounds in the presence of the $C_8$ and $C_9$ sulfosuccinates. Glutaraldehyde results are at 3 hours; DBNPA results are at 24 hours.

TABLE 2

Sulfosuccinate Enhancement of Glutaraldehyde and DBNPA[1]

| | Percent Inhibition of Growth | | |
|---|---|---|---|
| Surfactant (12 ppm) | 0 ppm Biocide | 2.5 ppm Glut | 5.0 ppm DBNPA |
| None | 0 | 3.5 | 14.0 |
| C4-sulfosuccinate | −5.0 | 2.0 | 8.0 |
| C5-sulfosuccinate | −3.0 | 5.0 | 19.0 |
| C6-sulfosuccinate | −4.0 | 5.0 | 15.0 |
| C8-sulfosuccinate | −5.0 | 19.0 | 24.0 |
| C9-sulfosuccinate | 3.0 | 15.0 | 31.0 |
| C13-sulfosuccinate | 0.6 | 1.0 | 19.0 |

[1]Negative numbers indicate a growth of the bacterial population
glut = glutaraldehyde
DBNPA = 2,2-dibromo-3-nitrilopropionamide Table 3 demonstrates the enhancement of inhibition of growth of bacteria observed with dithiol. The dithiol active is a fast acting biocide that dissipates rapidly. Therefore, although it is effective quite quickly, it may allow for the regrowth of the bacterial population after the biocide active dissipates. It is interesting to note that the $C_8$ and $C_9$ sulfosuccinates were effective at enhancing the longevity of the biocide's activity.

TABLE 3

Sulfosuccinate Enhancement of Dithiol Activity[1]

| | Percent Inhibition of Growth | |
|---|---|---|
| Surfactant (12 ppm) | 4 hours | 24 hours |
| 0 ppm biocide | | |
| None | 0 | 0 |
| C4-sulfosuccinate | −5.0 | 4.0 |
| C5-sulfosuccinate | −3.0 | 5.0 |
| C6-sulfosuccinate | −4.0 | −5.0 |
| C8-sulfosuccinate | −5.0 | 4.0 |
| C9-sulfosuccinate | 3.0 | −2.0 |
| C13-sulfosuccinate | 0.6 | −17.0 |
| 1.25 ppm dithiol | | |
| None | 45.0 | −46.0 |
| C4-sulfosuccinate | 42.0 | −38.0 |
| C5-sulfosuccinate | 58.0 | −10.0 |
| C6-sulfosuccinate | 40.0 | −68.0 |
| C8-sulfosuccinate | 39.0 | 3.0 |
| C9-sulfosuccinate | 52.0 | 6.0 |
| C13-sulfosuccinate | 37.0 | −23.0 |
| 2.5 ppm dithiol | | |
| None | 83.0 | 42.0 |
| C4-sulfosuccinate | 86.0 | −36.0 |
| C5-sulfosuccinate | 93.0 | −14.0 |
| C6-sulfosuccinate | 83.0 | −71.0 |
| C8-sulfosdccinate | 70.0 | 2.0 |
| C9-sulfosuccinate | 67.0 | 10.0 |
| C13-sulfosuccinate | 61.0 | −15.0 |
| 5 ppm dithiol | | |
| None | 99.0 | 12.0 |
| C4-sulfosuccinate | 99.0 | 15.0 |
| C5-sulfosuccinate | 99.0 | 9.0 |
| C6-sulfosuccinate | 99.0 | −41.0 |
| C8-sulfosuccinate | 99.0 | 24.0 |
| C9-sulfosuccinate | 96.0 | 45.0 |
| C13-sulfosuccinate | 96.0 | 8.0 |

[1]Negative numbers indicate a growth of the bacterial population
dithiol = 5-oxo-3,4-dichloro-1,2-dithiol As noted above, amounts of the treatment of the present invention as low as from about 1–5 ppm of the surfactant may be effective, in combination with the biocide, which concentration could vary widely, depending on e.g., process conditions, target organisms and/or the nature of the biocide. Furthermore, other aqueous systems such as metal working and oil and gas systems will also benefit from the present invention.

While we have shown and described herein certain embodiments of the present invention, it is intended that there be covered as well any change or modification therein which may be made without departing from the spirit and scope of the invention.

We claim:

1. A method for enhancing a treatment containing a biocidal compound to control the growth of microbes in an aqueous system which comprises adding to said system an effective amount of a dinonylsulfosuccinate surfactant, wherein the growth of microbes in said system is controlled while the amount of biocidal compound is decreased, said biocidal compound selected from the group consisting of an isothiazolinone compound, a bromonitropropanediol compound, 2, 2-dibromo-3-nitriloproprionamide, 5-oxo-3, 4-dichloro-1, 2-dithiol and glutaraldehyde.

2. The method as recited in claim 1 wherein at least about 1 ppm of the dinonylsulfosuccinate surfactant is added to the aqueous system.

3. The method as recited in claim 1 wherein said microbes comprise bacteria.

4. The method as recited in claim 1 wherein said microbes comprise fungi.

5. The method as recited in claim 1 wherein said aqueous system comprises a cooling water system.

6. The method as recited in claim 1 wherein said aqueous system comprises a pulping or papermaking system.

7. The method as recited in claim 1 wherein said aqueous system comprises a metal working system.

8. The method as recited in claim 1 wherein said aqueous system comprises an oil and gas system.

9. A method for enhancing a treatment containing a biocidal compound to control the growth of microbes in an aqueous system which comprises adding to said system an effective amount of a dioctylsulfosuccinate surfactant, wherein the growth of microbes in said system is controlled while the amount of biocidal compound is decreased, said biocidal compound selected from the group consisting of a mixture of 5-chloro-2-methyl-4-isothiazolin-3-one and 2-methyl-4-isothiazolin-3-one, a bromonitropropanediol compound, 2,2-dibromo-3-nitriloproprionamide, 5-oxo-3,4-dichloro-1,2-dithiol and glutaraldehyde.

10. The method as recited in claim 9 wherein at least about 1 ppm of the dioctylsulfosuccinate surfactant is added to the aqueous system.

11. The method as recited in claim 9 wherein said microbes comprise bacteria.

12. The method as recited in claim 9 wherein said microbes comprise fungi.

13. The method as recited in claim 9 wherein said aqueous system comprises a cooling water system.

14. The method as recited in claim 9 wherein said aqueous system comprises a pulping or papermaking system.

15. The method as recited in claim 9 wherein said aqueous system comprises a metal working system.

16. The method as recited in claim 9 wherein said aqueous system comprises an oil and gas system.

\* \* \* \* \*